(12) United States Patent
Taylor et al.

(10) Patent No.: US 7,250,619 B2
(45) Date of Patent: Jul. 31, 2007

(54) POWERED STERILE SOLUTION DEVICE

(75) Inventors: Michael A. Taylor, Napa, CA (US);
Mark L. Sizelove, Napa, CA (US);
Tralance O. Addy, Coto de Caza, CA (US)

(73) Assignees: PrisMedical Corporation, American Canyon, CA (US); Water Health International, Inc., Lake Forest, CA (US)

( * ) Notice: Subject to any disclaimer, the term of this patent is extended or adjusted under 35 U.S.C. 154(b) by 0 days.

(21) Appl. No.: 10/478,908

(22) PCT Filed: May 14, 2002

(86) PCT No.: PCT/US02/15325

§ 371 (c)(1),
(2), (4) Date: Jul. 14, 2004

(87) PCT Pub. No.: WO02/091986

PCT Pub. Date: Nov. 21, 2002

(65) Prior Publication Data

US 2004/0232079 A1    Nov. 25, 2004

(51) Int. Cl.
*B01D 61/08* (2006.01)
(52) U.S. Cl. .................. 250/504 R; 210/232; 604/83; 604/85
(58) Field of Classification Search ............... 210/232, 210/638; 422/261
See application file for complete search history.

(56) References Cited

U.S. PATENT DOCUMENTS

| | | | |
|---|---|---|---|
| 2,504,349 A | 4/1950 | Prieto | |
| 3,276,458 A | 10/1966 | Iversen et al. | |
| 3,491,234 A | 1/1970 | Wiltrout | |
| 3,517,816 A | 6/1970 | Huppen | |
| 3,562,520 A | 2/1971 | Hippen | |
| 3,710,111 A | 1/1973 | Collura | |
| 3,730,349 A | 5/1973 | Herrmann | |
| 3,836,781 A | 9/1974 | Ellison | |
| 3,858,048 A | 12/1974 | Shand et al. | |
| 4,070,289 A | 1/1978 | Akcasu | |
| 4,102,645 A | 7/1978 | Meacham, Jr. et al. | |
| 4,160,727 A | 7/1979 | Harris, Jr. | |
| 4,196,081 A | 4/1980 | Pavia | |
| 4,201,916 A | 5/1980 | Ellner | |
| 4,231,872 A | 11/1980 | Keil | |
| 4,277,332 A | 7/1981 | Baughn | |
| 4,280,912 A | 7/1981 | Berry, III et al. | |
| 4,304,996 A | 12/1981 | Blades | |
| 4,396,383 A | 8/1983 | Hart | |
| 4,458,733 A | 7/1984 | Lyons | |
| 4,484,920 A | 11/1984 | Kaufman et al. | |
| 4,495,067 A | 1/1985 | Klein et al. | |
| 4,507,114 A | 3/1985 | Bohman et al. | |

(Continued)

*Primary Examiner*—David A. Vanore
(74) *Attorney, Agent, or Firm*—Knobbe Martens Olson & Bear LLP (57) ABSTRACT

The disclosure below relates to apparatus and methods for producing medicament using sub-optimal water sources. One embodiment of the disclosure is directed to an apparatus comprising a preliminary purification component, a disinfection component, a pharmaceutical grade water preparation (PGW) component, and a drug pack. Another disclosed embodiment relates to a method for producing a peritoneal dialysis solution, comprising, passing diluent through a preliminary purification component, passing diluent through a disinfection component, passing diluent through a PGW preparation component, passing diluent through a drug pack, and collecting solute produced by the drug pack.

24 Claims, 6 Drawing Sheets

U.S. PATENT DOCUMENTS

| | | | |
|---|---|---|---|
| 4,576,603 A | 3/1986 | Moss | |
| 4,622,465 A | 11/1986 | Harig et al. | |
| 4,629,896 A | 12/1986 | Bridgen | |
| 4,648,978 A | 3/1987 | Makinen et al. | |
| 4,661,264 A | 4/1987 | Goudy, Jr. | |
| 4,698,153 A | 10/1987 | Matsuzaki et al. | |
| 4,742,231 A | 5/1988 | Bridgen | |
| 4,756,838 A | 7/1988 | Veltman | |
| 4,784,763 A | 11/1988 | Hambleton et al. | |
| 4,810,388 A | 3/1989 | Trasen | |
| 4,871,463 A | 10/1989 | Taylor et al. | |
| 4,899,057 A | 2/1990 | Koji | |
| 4,909,931 A | 3/1990 | Bibi | |
| 4,994,056 A | 2/1991 | Ikeda | |
| 5,004,535 A | 4/1991 | Bosko et al. | |
| 5,032,265 A | 7/1991 | Jha et al. | |
| 5,059,317 A | 10/1991 | Marius et al. | |
| 5,071,558 A | 12/1991 | Itob | |
| 5,084,558 A | 1/1992 | Rausch et al. | |
| 5,110,479 A | 5/1992 | Frommer et al. | |
| 5,128,035 A | 7/1992 | Clack et al. | |
| 5,186,830 A | 2/1993 | Rait | |
| 5,217,607 A | 6/1993 | Dalton, III et al. | |
| 5,227,053 A | 7/1993 | Brym | |
| 5,230,792 A | 7/1993 | Sauska et al. | |
| 5,259,954 A | 11/1993 | Taylor | |
| 5,264,555 A | 11/1993 | Shorr et al. | |
| 5,288,412 A | 2/1994 | Voorhees et al. | |
| 5,366,705 A | 11/1994 | Reidy | |
| 5,387,804 A | 2/1995 | Suzuki et al. | |
| 5,395,323 A | 3/1995 | Berglund | |
| 5,420,432 A | 5/1995 | Manook et al. | |
| 5,441,179 A | 8/1995 | Marsh | |
| 5,494,585 A | 2/1996 | Cox | |
| 5,503,800 A | 4/1996 | Free | |
| 5,536,403 A | 7/1996 | Sugimoto | |
| 5,545,335 A | 8/1996 | Sween et al. | |
| 5,584,990 A | 12/1996 | Sugimoto | |
| 5,597,482 A | 1/1997 | Melyon | |
| 5,597,487 A | 1/1997 | Vogel et al. | |
| 5,628,895 A | 5/1997 | Zucholl | |
| 5,632,890 A | 5/1997 | Sugimoto | |
| 5,635,133 A | 6/1997 | Glazman | |
| 5,660,719 A | 8/1997 | Kurtz et al. | |
| 5,685,980 A | 11/1997 | Patapoff et al. | |
| 5,725,762 A | 3/1998 | Beal et al. | |
| 5,725,777 A | 3/1998 | Taylor | |
| 5,766,479 A | 6/1998 | Collentro et al. | |
| 5,780,860 A | 7/1998 | Gadgil et al. | |
| 5,843,304 A | 12/1998 | Marchesseault et al. | |
| 5,843,309 A | 12/1998 | Mancil | |
| 5,868,924 A * | 2/1999 | Nachtman et al. | 210/85 |
| 5,877,392 A | 3/1999 | Russell et al. | |
| 5,900,212 A | 5/1999 | Maiden et al. | |
| 5,951,876 A | 9/1999 | Snowball | |
| 6,031,241 A | 2/2000 | Silfvast et al. | |
| 6,156,192 A | 12/2000 | Rummier | |
| 6,156,210 A | 12/2000 | Sadkhin | |
| 6,200,466 B1 | 3/2001 | Bender | |
| 6,348,151 B1 | 2/2002 | Kunkel | |
| 6,419,821 B1 | 7/2002 | Gadgil et al. | |
| 6,719,745 B1 | 4/2004 | Taylor | |

\* cited by examiner

POWERED STERILE SOLUTION DEVICE

BACKGROUND OF THE INVENTION

1. Field of the Invention

The apparatus and methods disclosed herein relate to the preparation of sterile water for various medical uses. An exemplary medical use is the preparation of peritoneal dialysate solutions or hydration fluids under sub-optimal conditions.

2. Description of the Related Art

The preparation of medicaments in the field or under sub-optimal conditions is complicated by the absence of clean water supplies. Existing water purification devices that produce pharmaceutical grade water (PGW) in remote locations have limited production capacity, both by limiting flow rates and by reducing product life span. The purification capacity of such devices can become severely limited when used to purify significantly contaminated water sources. In fact, even potable water quality standards for municipal water treatment throughout the developed world allow widely variable levels of contamination that render such water supplies unsuitable for use in the preparation of medicaments, without further purification.

Effective water purification to a level that meets pharmaceutical-grade water (PGW) quality standards typically requires extensive mechanical, filtration, chemical, and other forms of manipulation. Disinfection alone is not adequate to achieve PGW. Elevated levels of dissociable ions are acceptable in municipally treated waters for drinking but are potentially hazardous to health if administered in non-physiologic levels. The by-products of microbial contamination even following Disinfection are potentially life threatening. Endotoxins derived from gram negative bacteria represent a life threatening hazard resulting from pyrogenic shock. A number of common water contaminants are discussed below.

Particulate Contamination

PGW have limits that do not apply to potable water standards maximal potable water standards for particulate matter severely limits the capacity of remote site PGW purification systems.

Organics Contamination

The acceptable levels of organic contaminants in drinking water may exceed acceptable levels in a therapeutic PGW due to the potential toxicity of intravenous administration of these agents. The toxicology associated with ingested agents is a function of the blood level reached following absorption into the blood stream. With therapeutic solutions produced from PGW, the amount of organic contaminants associated with the PGW is the blood level. Therefore, exhaustive purification beyond drinking water quality is necessary to mitigate the potential toxicity. This problem is exacerbated with the use of available water with uncontrolled organic contamination. Without preliminary removal of organic contaminants, a PGW system would have severely reduced purification capacity.

Deionization

Dissolved solids constitute a significant contaminant in water. These agents include salts, most commonly in the form of sodium chloride. Dissolved solids also include inorganic contaminants including heavy metals, such as arsenic, mercury, lead, and iron. As with removal of organic contaminants, the toxicology of these agents is markedly increased with direct administration into the blood stream. The deionization capacity of a PGW system would be markedly limited without preliminary deionization of the source water.

Disinfection

Perhaps the greatest acute hazard to ingestion of available water results from the potentially infectious agents that may be present therein. The most effective preventative measure to combat this hazard involves the disinfection of the source water.

Among the potentially infectious agents that must be removed from source water include viruses, bacteriological agents, spore-forming parasites, and fungal agents. The larger of these agents are readily filtered from source water. Some microbial agents, however, have the capacity to grow through filters, thus rendering them non-sterile. Moreover, viruses pass through microfilters, therefore requiring the use of ultrafilters or reverse osmosis filtration. These forms of filtration require expansive mechanical generation of high pressure and thus entail an extensive power requirement.

Drinking water disinfection devices are capable of rendering viruses and microbes inactive and non-replicative. These devices, however, do not remove these agents or cell debris from the product water. In situations where the water is intended for drinking, the point is not of great importance because generally viruses, bacteria, bacterial by-products, spores, or other microbiological materials if killed or rendered non-replicative, do not represent potential hazards.

For production of water-based, injectable fluids, bacterial-by products represent a significant hazard and must be removed to prevent pyrogenic shock and potential death. The purification capacity of PGW systems is limited, without a preliminary filtration of these agents in combination with a Disinfection step, which renders the microbial agents non-replicative.

SUMMARY OF THE INVENTION

The disclosure below relates to apparatus and methods for producing medicament using sub-optimal water sources. One embodiment of the disclosure is directed to an apparatus comprising a preliminary purification component, a Disinfection component, PGW preparation component, and a drug pack. Another disclosed embodiment relates to a method for producing a peritoneal dialysis solution, comprising, passing diluent through a preliminary purification component, passing diluent through a Disinfection component, passing diluent through a PGW preparation component, passing diluent through a drug pack, and collecting solute produced by the drug pack.

DETAILED DESCRIPTION OF THE PREFERRED EMBODIMENT

While the illustrated embodiments are described in the context of particular formulations and relative proportions of reagents, the skilled artisan will find application for the described methods and devices in a variety of different formulations and proportions of reagents. Examples of these uses and solutions include, but would not be limited to, sterile water for injection or irrigation, sterile solution diluent for intravenous solutions, vaccines, oral re-hydration solutions, medical grade drinking water and intravenous drug delivery.

The apparatus and methods disclosed below provide the means by which to purify otherwise unpurified water available from the vast majority of water sources to a level of quality sufficiently high (pharmaceutical grade) for use in production of medical therapeutic solutions, then utilizes reagent delivery components to produce therapeutic solutions. A preferred embodiment consists of a preliminary filtration component, a purification component, and disinfection component. Functioning together, each component renders available fresh water to be purified to produce medical quality water.

One novel aspect of the disclosed invention relates to the range of possible uses of selected components to meet particular needs. This range includes the preparation of drinking water to the preparation of patient specific, sterile, therapeutic solution production. The modular nature of the disclosed components provides a spectrum of preventative and therapeutic measures for water-born illnesses and delivery on medicaments under less than optimal circumstances, such as in a rural setting. Water disinfection and decontamination for production of delivered fluids such as oral re-hydration solution, the drug pack can be attached tot he preliminary disinfection component. Such an embodiment enables the production of electrolyte solutions or nutritional solutions for infants or immuno-compromised individuals. The additional purification provided by the PGW maker allows for the production of highly purified water suitable for immuno-compromised patients and others particularly sensitive to foreign matter. This highly purified water can also be used for remote site production of water of sufficient quality for injectability, including product waters intended for subsequent production of dialysate solutions or intravenous solutions. By addition of the drug pack component, reagents could be added to injectable quality waters to produce general use therapeutic solutions such as sterile physiologic saline, Lactated Ringer's, sterile saline with dextrose or other crystalline or colloid containing resuscitation fluids. The injectable quality waters could be used as diluents for injectable drugs or vaccines delivered from drug packs. The drug packs components could also be used to augment injectable quality water with combinations of reagents to produce peritoneal or hemodialysate solutions in remote locations. By additional of combinations of drug packs components to the system, patient specific therapeutic solutions could be prepared, such as nutritionals and/or anti-infectives in patient specific doses.

In particular, medical quality water or other fluid produced by the illustrated water purification pack 12 exhibits the following characteristics: a very low level of total organic carbon, preferably less than about 1 ppm and more preferably less than about 500 ppb; low conductivity, preferably less than about 5.0 microSiemens (2.5 ppm) and more preferably less than about 2.0 microSiemens (1 ppm TDS); near neutral pH, preferably between about 4.5 and 7.5, and more preferably between about 5.0 and 7.0; very low particulate concentration, preferably fewer than less than about 12 particles/mL of particles less than 10 micron more preferably less than about 6 particles/mL of such particles, and preferably less than about 2 particles/mL of particles less than 25 micron more preferably less than about 1 particle/mL of such particles; and low endotoxin levels, preferably less than about 0.25 endotoxin units (EU) per mL (0.025 ng/mL), more preferably less than about 0.125 EU/mL.

Figure 1:
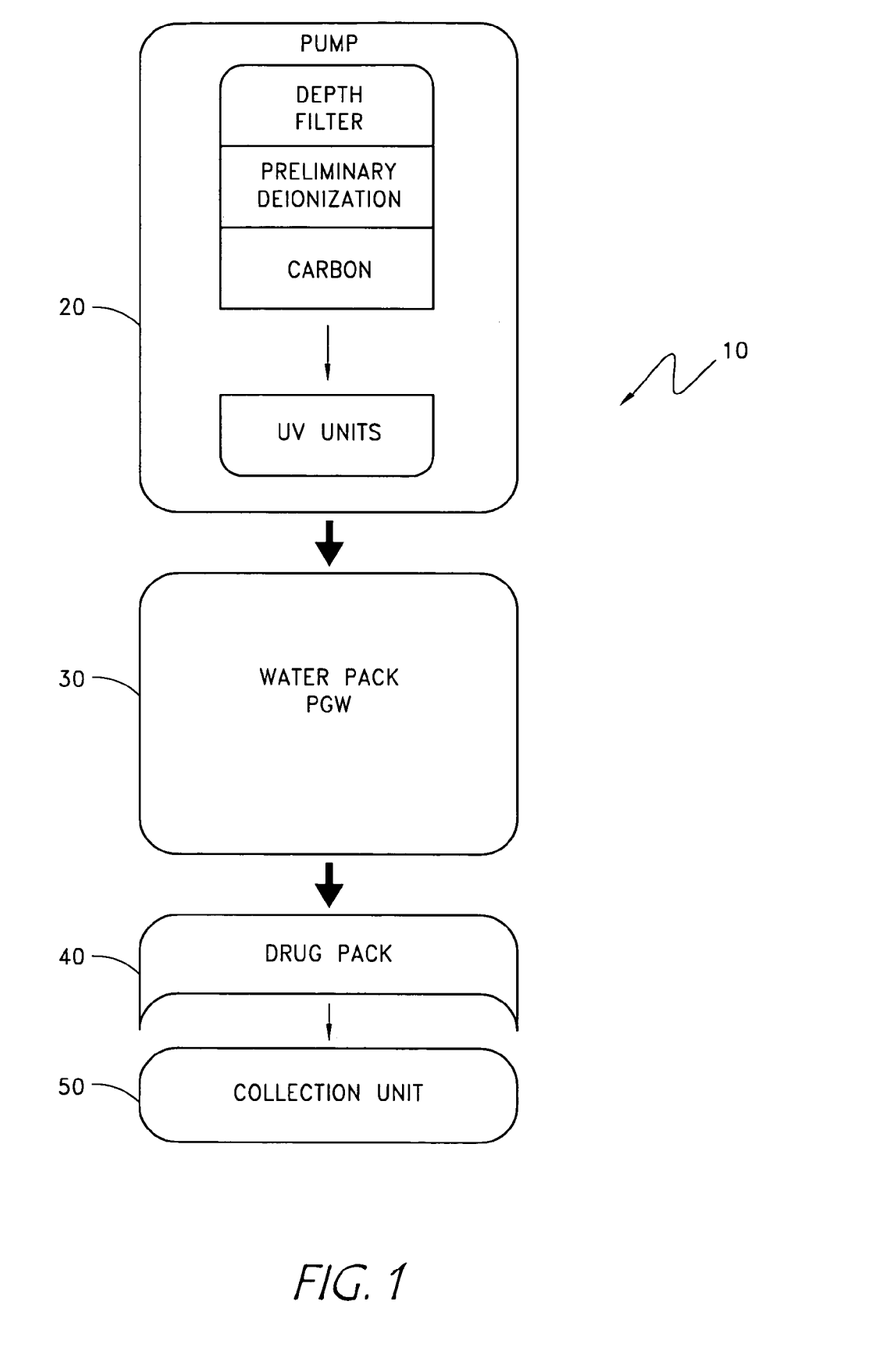
FIG. 1 is a flow chart of the medicament preparation system.

FIG. 1 depicts a therapeutic solution system 10, shown in three general components. The first component of the system is a preliminary purification and Disinfection component 20. The second component of the system is typically a PGW production component 30, which produces pharmaceutical grade water from the water produced from the preliminary purification and Disinfection component. The third component of the system is typically a therapeutic solution component or a drug pack 40, which utilizes dry reagent to produce a medicament solution suitable for therapeutic administration. An optional collection unit 50 can be included in the system to provide a means of aseptic/sterile solution collection.

Preliminary Purification and Disinfection Component

Preferably, the preliminary purification and disinfection component filters and purifies sea water, brackish water, ordinary tap water, or fresh water from some other source provides a first stage of water purification. Typically, this is done using an optional pump and filtration assembly or by gravity. Additionally, the preliminary purification and disinfection component decontaminates the source water to prepare it for passage to the PGW production component of the system. These components preferably reduce the load on the downstream PGW unit, discussed below. An exemplary disinfecting component is described in U.S. Pat. No. 5,780,860, entitled, "UV WATER DISINFECTOR." In this example, the UV lamp is positioned down stream of the preliminary filtration device.

The disinfection unit taught in U.S. Pat. No. 5,780,860, functions as a gravity driven disinfecting apparatus. The presently described apparatus can use gravity or other means to drive the fluid past the disinfecting means. Further, although UV disinfection is a preferred embodiment, other means of germicide are contemplated for use with in the described apparatus.

The basic structures of a typical preliminary purification component provide a continuous stream of purified water. Typically, a pump provides water to an entry feed trough directing the feed water to an inlet port. In some embodiments, the inlet port is about 1.5 cm in diameter when the inlet water flow rate is about 15 liters/minute. In other embodiments, the inlet port is about 3 cm in diameter when the inlet water flow rate is about 60 liters/minute. The feed water proceeds into the inlet manifold through a distribution tube. The water flowing through this assembly is essentially the same pressure throughout the entry chamber. The feed water then enters the treatment chamber through a perforated baffle wall, which laminarizes the flow. Angled or baffled sides ensure uniform UV exposure. A UV lamp suspended above the flow treats the feed water, and the pure water cascades over an outlet baffle weir into the outlet manifold and directly into a collection vessel, or into a holding tank from which the water is distributed to the users.

The structure of the entry feed trough provides water to the UV disinfection device via a pump, at a steady rate which never exceeds the safe disinfection capacity of the unit. The inlet port is calibrated so that excess force of feed water will result in back pressure, resulting in a reduction of flow through the unit. If there is an interruption in power, causing the UV lamp to temporarily cease function, a solenoid operated safety valve in the inlet manifold temporarily blocks the entry of feed water. In a preferred embodiment, gravity drives the water over the UV treatment tray. Other safety features have also been built into the inventive device.

Preferably, the water flow rate into the UV light disinfection unit is limited to ensure adequate UV disinfection. Generally, as the flow rate decreases, the quality of the UV disinfection is enhanced, due to the fact that the water is exposed to the light from the UV lamp for a longer duration and thus receives more UV energy. Therefore, the flow rate is preferably low enough to ensure that the water receives adequate UV light exposure. If desired, a flow-restrictor or flow-limiter may be included upstream of the UV light disinfection unit to ensure that the flow rate is below a certain level.

The baffle wall and exit baffle before and after the treatment chamber provide for steady, predictable treatment of all portions of the feed water. Angling of the treatment chamber tray, and positioning of the UV lamp and reflectors, assures that even water most distant from the lamp receives close to the same UV dosage as that nearest the lamp.

To assure the safety of the user, the power to the UV lamp cuts off if its protective housing is opened, so that there is no accidental direct exposure to the UV light. While a ground wire is provided to avoid the potential for shock, there is also a Ground Fault Circuit Interrupt (GFCI) provided which will cut off power whenever a short occurs.

The UV light disinfection unit treats the water stream by emitting UV light onto the water as it flows through the unit. Preferably, the unit emits UV light in the wavelength range 240 to 280 nanometers (nm), which is known to be germicidal. The UV exposure causes adjacent bases in the DNA to covalently bond together, thus disabling it from replication. Preferably, the unit includes a low-pressure mercury arc (the same as that used inside ordinary kitchen fluorescent lamps), which puts out 95% of its energy at 254 nanometers and is thus an extremely efficient germicidal UV source.

In a preferred embodiment, the UV light disinfection unit 36 comprises a UV unit, as described by Gadgil '860. The UV unit includes a linear UV lamp positioned horizontally below a semi-cylindrical polished aluminum reflector, suspended above the free surface of water flowing in a shallow stainless steel tray. This design innovation circumvents the problem of chemical- and bio-fouling of the solid surface between the UV source and the water by eliminating any such surface. Also, since the flow resistance is small, water with pressure of only a few centimeters of water column can flow through the device. The UV unit consumes 60 watts of electricity, disinfects just under 1 ton of water per hour (15 lpm, more than twice the flow rate through an average U.S. bathtub faucet) by delivering it a UV energy dose of up to 110,000 microwatt-seconds/cm$^2$ in 10-12 seconds, and accepts atmospheric-pressure raw water (e.g., poured from a hand-carried pot). In the emergency relief system, therefore, water is gravity-driven through the UV disinfection unit, rather than pressurized.

Figure 2:
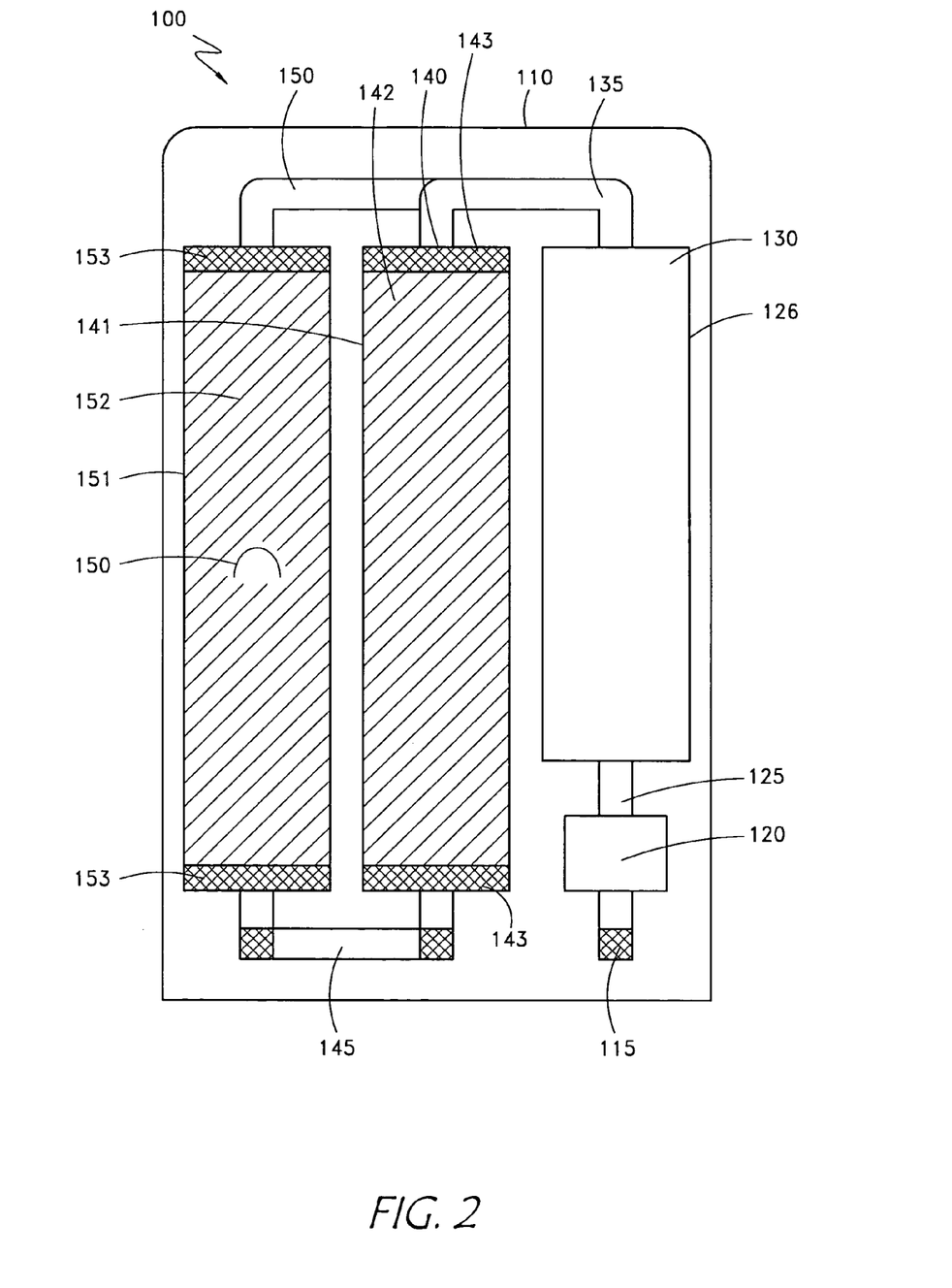
FIG. 2 is a rear view of a medical fluid delivery device.

FIG. 2 shows a rear view of an exemplary preliminary purification and Disinfection component. This view shows the preliminary purification portion of the system. Typically, the preliminary purification of the system 100 comprises a housing 110, from which an inlet tube 115 extends. Generally, the inlet tube comprises a connection site for available source water.

A pump 120 is shown connected to the inlet tube. This water is propelled into system by the pump. The pump may be eliminated or left inoperative if a pressurized water source is available. The pump is a low power requiring device that provides adequate power to pressurize the system. The pressure derived from this pump typically ranges from 1 to 20 pounds per square inch (PSI), preferably between 1 and 10 PSI, and more preferably between 2 and 5 PSI.

The pump is preferably connected to a depth filtration component 125 by a depth filter tube 130. The depth filtration component comprises a closed housing 126. Typically, the housing consists of any chemically inert material, including polymers, including polypropylene and polyethylene and glass. The housing contains torturous paths of controlled pore size to retain insoluble particulate materials greater than 1 micron, while having sufficient depth to prevent significant pressure increases until the filter becomes saturated with particulates. This component is held in place by retention clips that enable rapid removal and replacement of the deionization component 125. The connection tubes for this component are sufficiently pliable to enable free insertion of the inlet and outlet connectors of the organic chemical reduction component.

The depth filtration component is connected to an organic chemical reduction component 140 by a connection tube 135. The organic chemical reduction component consists of a housing 141, an organic retention bed 142 and organic retention bed restraints 143. The organic reduction bed will generally consist of carbon-based purification materials, which are well known in the art. The organic retention bed restraints consist of any controlled pored material that has an absolute pore size of about less than 10 microns. These components can be held in place by retention clips, grooves, or other means that enable rapid removal and replacement. As discussed above, the connection tubes for this component are also sufficiently pliable to enable free insertion of the inlet and outlet connectors of the organic retention bed into the tubing.

A deionization component 150 is connected to the organic chemical reduction component by connection tube 145. The deionization component will generally consist of a housing 151, the deionization bed 152 and the resin bed restraints 153, which are generally composed of chemically inert materials. The deionization bed consists of a mixed bed of roughly comparable volumes of cation and anion exchangers. The bed restraints are generally composed of controlled pored, chemically inert materials that retain resin beads. The anion and cation components may be contained together or they may be separately held prior to a organic removal component followed by a mixed bed deionization component. Water exits through tube 155.

Figure 3:
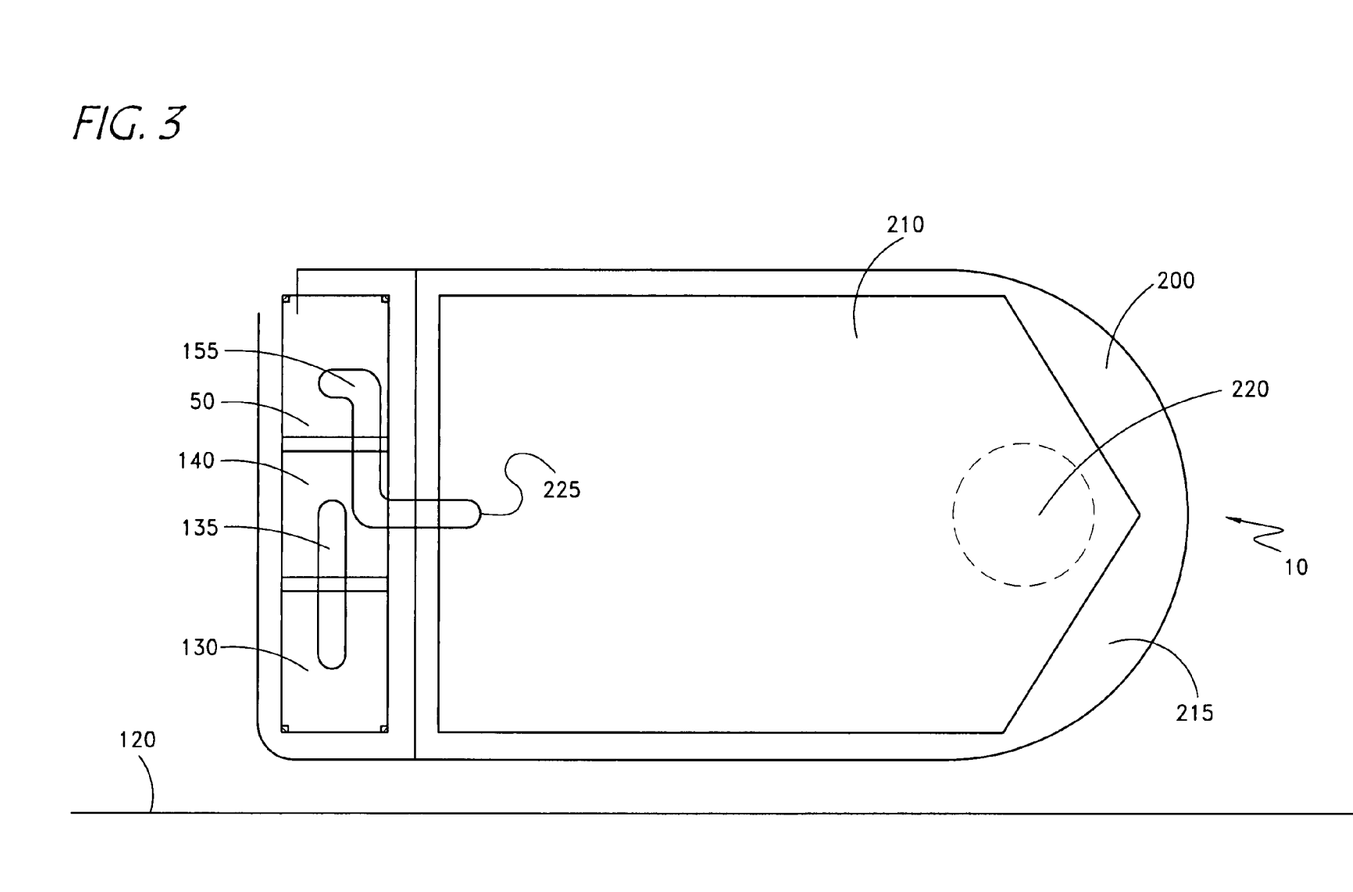
FIG. 3 is a top view of the device in accordance with FIG. 2.

FIG. 3 shows a top view of the system 10. This view illustrates the Disinfection component 200 of the system. The disinfection component will generally comprise a housing 215, the internal ultraviolet light 220, an inlet 225, a UV light containment structure 226, an outlet 227, and a light activation switch. Advantageously, the UV light is of low wattage and serves to decontaminate water pumped from the preliminary purification system 100 into the Disinfection component through the inlet. By treating the filtrate produced from the preliminary filtration system with UV light, any viruses or other microbial agents, are rendered non-replicative.

An exemplary disinfecting component is described in U.S. Pat. No. 5,780,860, entitled, "UV WATER DISINFECTOR."

Pharmaceutical Grade Water (PGW) Production Component

In a preferred embodiment, the PGW production component of the described system comprises a portable apparatus for purifying water to levels suitable for medical applications, including injection into the human body. In a more preferred embodiment, the water purified by the PGW production component will have been preliminarily purified and decontaminated. Such a preliminary step will increase the useful lifespan of the PGW production component and further insure the purity of the water produced from the PGW production component. A suitable PGW production component is disclosed in U.S. Pat. No. 6,719,745 entitled, "WATER PURIFICATION PACK."

The apparatus described herein contemplates the use of fewer components in the PGW production component since many of its functions are already performed by the preliminary filtration component. Alternatively, a complete PGW production component can be used. The use of a complete PGW component will increase the life span of the device.

Figure 4:
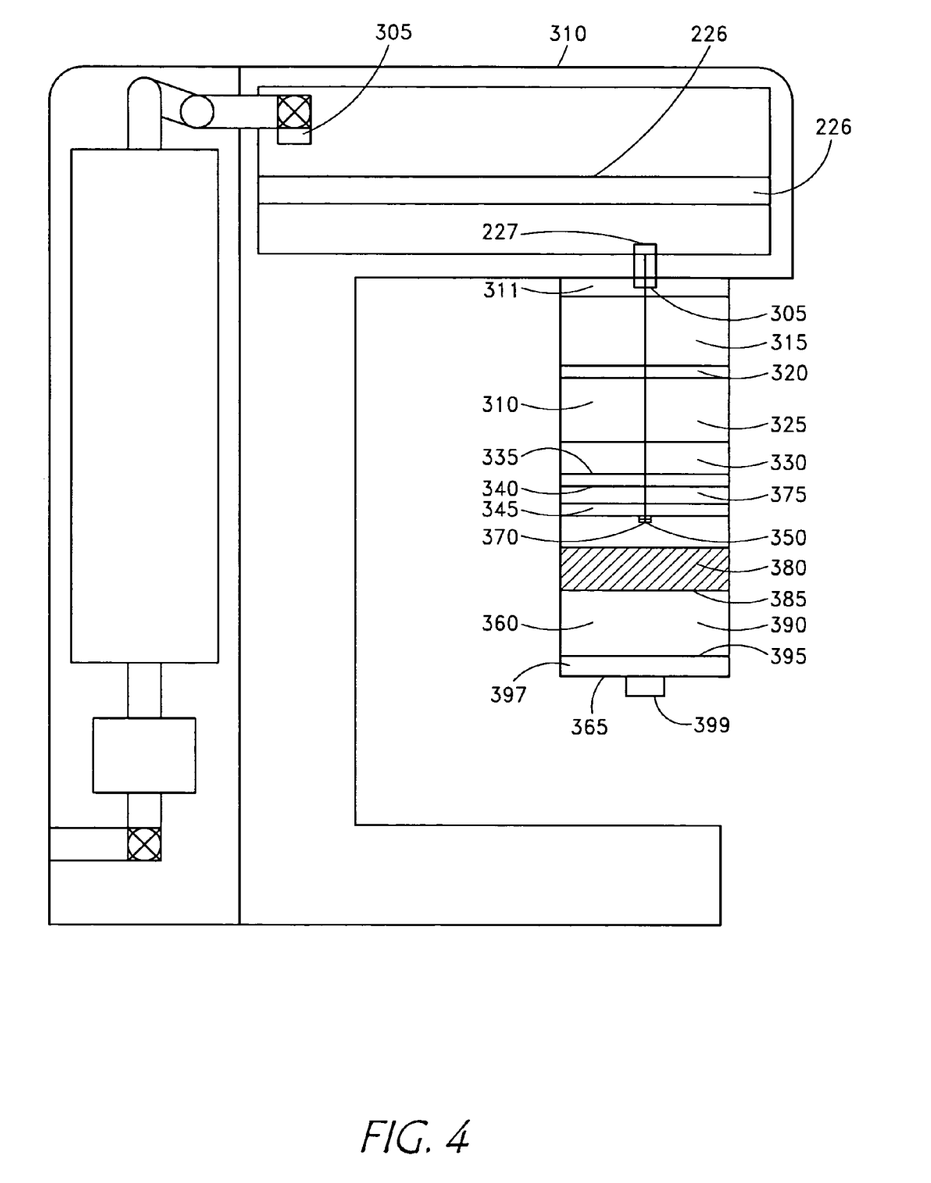
FIG. 4 is a side view of the device in accordance with FIG. 2.
Figure 5:
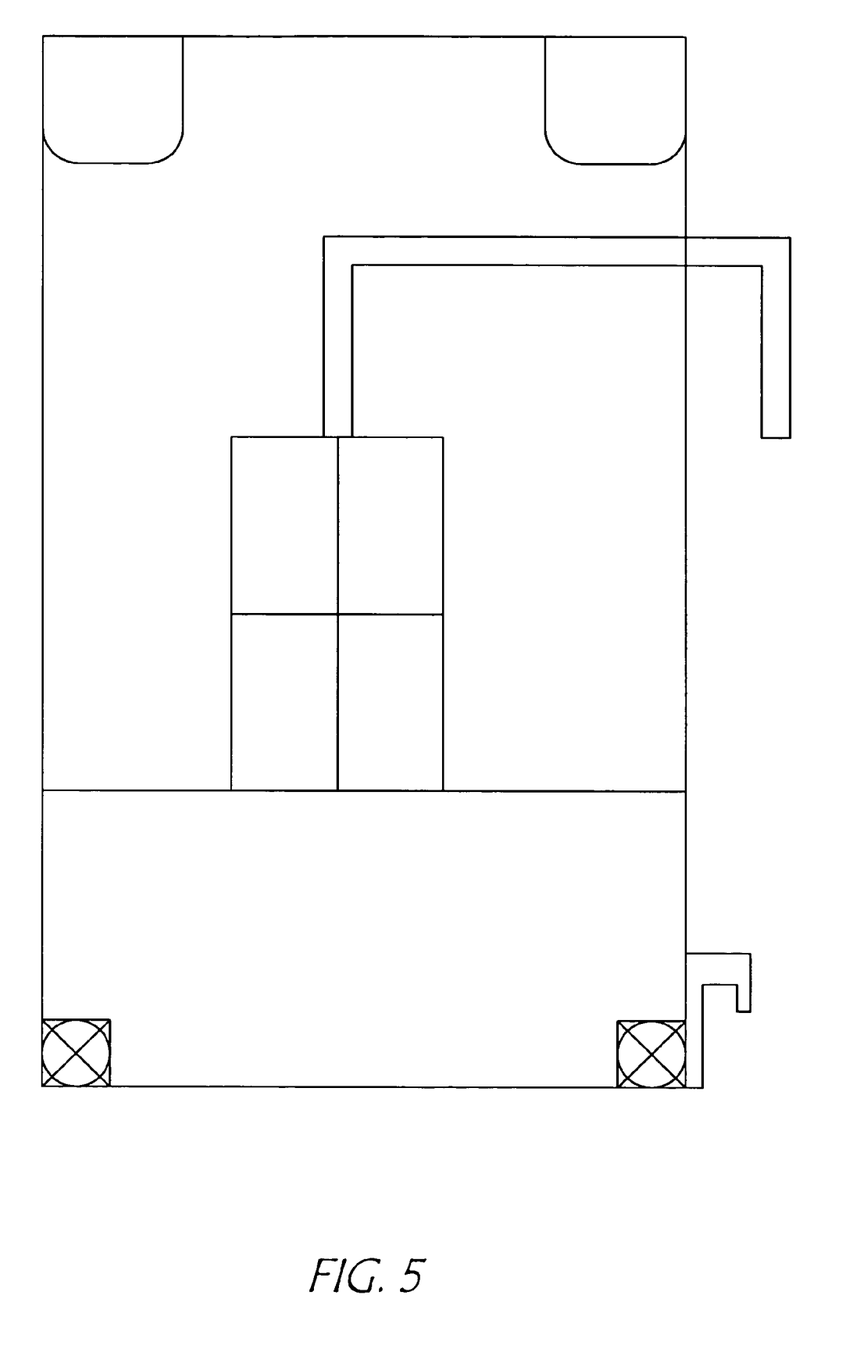
FIG. 5 is a bottom view of the device in accordance with FIG. 2.

FIG. 4 shows a side view of the system and illustrates the PGW production component. Typically, the PGW production component of the described system includes a housing 310, an inlet 305, fluid distribution channels 311, a compression component 315, a depth filtration component 320, a deionization component 325, an organic contaminant collection component 330, a microfiltration component 335, a microfilter support 340, fluid collection channels 345 and a housing outlet 350. Typically the microfiltration component will have a porosity of less than about 0.5 microns and is configured to retain endotoxins. Ultrafiltration membranes may be included in addition to or in place of the microfilter.

As water emerges from the Disinfection component of the system it is passed into the PGW production component. Passage through the components listed above provides pharmaceutical grade water for the preparation of medicinal compositions in the therapeutic solution component.

Therapeutic Solution Component

Having produced pharmaceutical grade water (PGW) using the system components described above, the PGW can be used to produce a variety of medicinal solutions. A variety of medicaments are contemplated for use with the described system. For example, solutions suitable for peritoneal dialysis can be prepared using the described system. An exemplary therapeutic solution component is described in U.S. Pat. No. 6,274,103 entitled, "APPARATUS AND METHOD FOR PREPARATION OF A PERITONEAL DIALYSIS SOLUTION."

Other methods of preparing medicaments are contemplated for use with the described system. For example, U.S. Pat. No. 6,605,214 entitled, "METHODS AND DEVICES FOR PREPARING HEMODIALYSIS SOLUTIONS," can also be used as a therapeutic solution component.

A preferred embodiment provides an apparatus for producing dialysis or intravenous solutions from dry reagents immediately prior to administration. The therapeutic component allows for the production of physiologically compatible dialysate or intravenous solutions and minimizes the likelihood of undesirable reactions among reagents. Moreover, the a typical dialysate producing component also facilitates separation of incompatible reagents. Both of these features, independently and in combination, result in a relatively simple and inexpensive apparatus for storing, transporting and producing solution from peritoneal dialysis reagents in dry form. Moreover, the devices and methods expand options for practically applicable solution formulations.

One exemplary medicament preparation device comprises a housing, which defines a fluid flow path through it. The therapeutic agent component 360 generally consists of a housing 365, an inlet 370, diluent distribution channels 375, agent compression component 380, agent retention frit 385, therapeutic agent bed 390, agent restraint bed 395, solution collection channels 397 and the outlet 399. The compression component 380 assists in the dissolution of the therapeutic agent bed and facilitates complete dissolution of the reagents contained therein. Typically, at least one reagent bed is kept within the housing along the fluid flow path.

Figure 6:
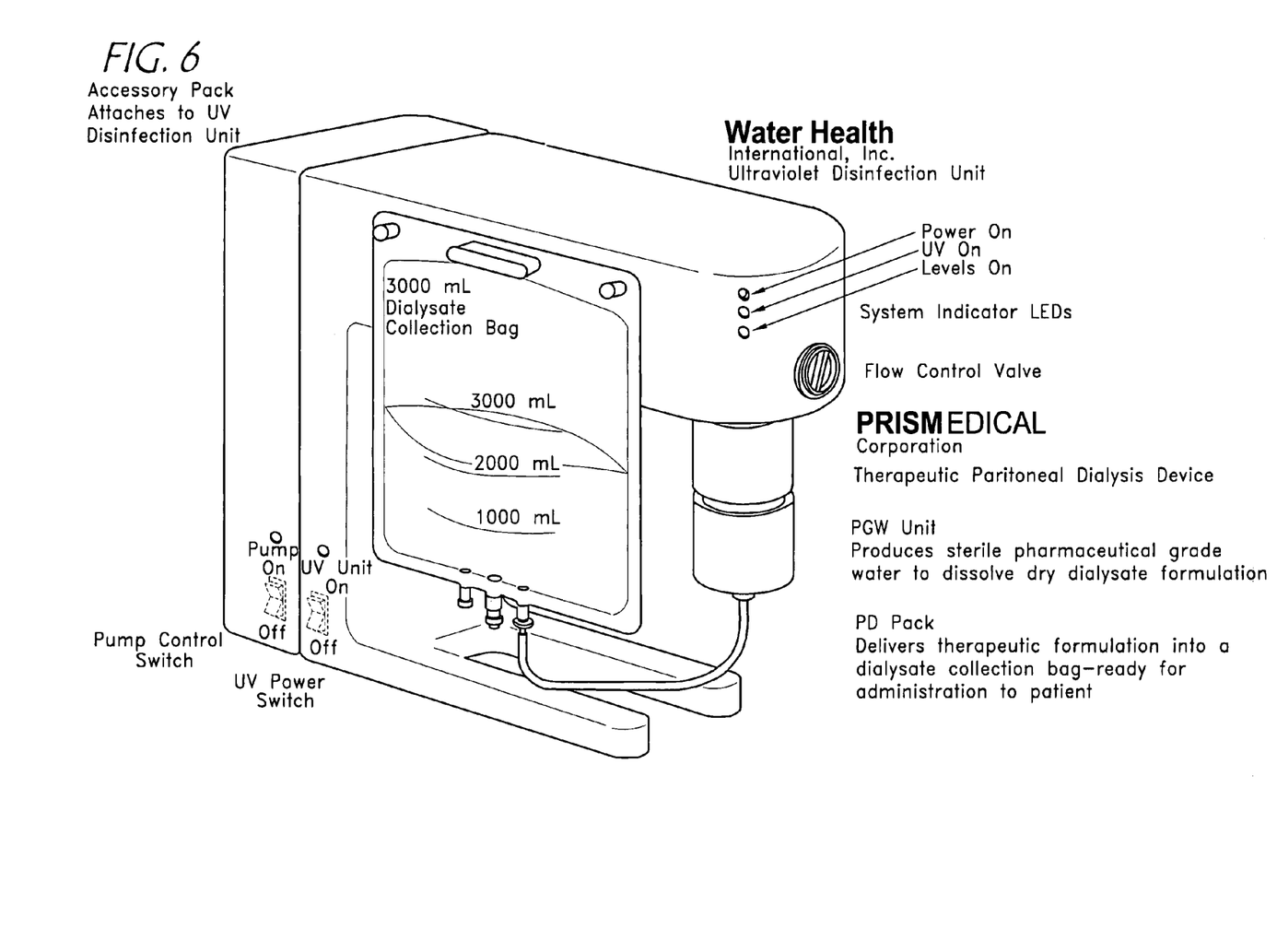
FIG. 6 is a isometric view of the ultraviolet disinfection unit, the PGW unit and the PD Pack attached together. A collection bag is also shown.

A collection device can also be provided as a component of the described system. A exemplary collection bag is shown in FIG. 6. The collection component includes the collection bag tubing, the intermediate microfilter and the collection bag. In one embodiment, the collection bag can be situated on the exterior of the system housing on the paired support hooks and a central positioning bar.

Mechanism of Action

The system described above comprises an apparatus and a method for Disinfection of source water rendering the viruses and other microbiological agents non-replicative. This mitigates the potential for microbiological grow through of filtering components. Non-replicative viruses need not be removed from product water because they do not represent an infectious hazard. The PGW capability augments the preliminary purification component capability and the Disinfection component in production of PGW from available water. The preliminary purification component capability and the disinfection component produce from potentially contaminated available water a decontaminated water that is aliquated for individual patient requirements.

The PGW further purifies this water to pharmaceutical quality. The PGW enables removal of agents that represent potential intravenous hazards. The therapeutic agent component provides a means of adding the required beneficial reagents to the PGW, producing the desired therapeutic solution. The method includes a means to produce intravenous solutions, dialysis solutions, nutritional solutions or other medicinal solutions in small to large volumes from any water based fluid, regardless of the quality of the source water. The collection component provides a collection reservoir for the prepared therapeutic solution.

Available water enters the preliminary purification component via the inlet 115. The system is pressurized by the pump 120. The initial component of the component is the depth filtration component 126. This component 126 retains insoluble materials greater than 1 micron. The connection tube 135 provides a means of conveying particulate free water to be carried to the organic chemical reduction component 140, which reduces organic materials in the source water. It also reduces biologicals and biological by-products, including endotoxin. The connection tube 145 to the deionization component 150 provides passage of partially decontaminated water to the next component. The deionization component retains dissociable ions, biological by-products and any contaminants containing charged materials. The outlet of preliminary purification component consists of a connection tube 155 and outlet providing connection to the Disinfection component 200. The preliminary purification component is activated by the component activation switch located on the component housing.

The partially purified water is pushed into the Disinfection component. When activated the ultraviolet light within the Disinfection chamber provides a means of rendering the water passing through the housing decontaminated. A reflective inner surface 226 within the Disinfection chamber enhance the Disinfection capability of the ultraviolet light and minimize the formation of biofilm on the ultraviolet light housing and the Disinfection chamber. In one embodiment, the internal volume of the Disinfection chamber is approximately 600 milliliters. With a flow rate of 100 ml/min this provides a 6 minute transit time through this component, which is more than adequate for decontamination.

The partially purified, decontaminated water is then pushed from the Disinfection chamber outlet into the therapeutic agent component inlet. Within this component water enters the inlet of the PGW purification component. Water is distributed within the housing via the fluid distribution channels. Adjacent to this component is compression component, which constrains the housing contents. The depth filtration component provides additional filtration of any particulates not removed by the preliminary purification component. The deionization component retains dissociable ions and other charged materials including endotoxin. The indicator light provides an indication that the water quality meets or exceeds the desired levels of dissolved solids or conductivity. The organic contaminant removal component removes residual organics not removed by the preliminary purification component. The microfiltration component and the microfilter support function to prevent penetration of particles greater than 0.2 microns. This includes bacteria and other microbes. Chemical modification of the microfilter enables additional retention of any charged materials, including endotoxin. The PGW prepared by this component collects within the fluid collection channels and exits the PGW purification component via the housing outlet.

PGW enters the therapeutic agent component via the inlet. The PGW is distributed through out the housing via the diluent distribution channels. The PGW then passes through the porous agent compression component, which serves to constrain the housing contents. The agent retention frit has pores of sufficiently small size to prevent penetration of undissolved particles. Diluent passes freely through this frit and contacts the therapeutic agent bed inducing dissolution of this bed. The downstream agent restraint frit retains the therapeutic agent particles of the therapeutic agent bed until they are dissolved. The prepared solution passes through this frit into the solution collection channels and pass out the outlet, which is continuous with the collection bag tubing. An intermediate microfilter provides additional assurance of sterility of the solution exiting the system. The collection bag provides a means of sterile capture of the prepared therapeutic solution while maintaining sterility. The types of therapeutic solutions that can be produced by the system includes sterile water for injection and irrigation; intravenous solution including sterile physiologic saline lactated ringer's solution, saline with dextrose, dialysate solutions including peritoneal and hemo-dialysate; nutritional solutions; oral rehydration solutions; and diluent for vaccines pharmaceuticals and other medicaments.

The apparatus provides a system capable of producing a wide range of injectable quality, therapeutic solutions in any location from the water available at the location the solution is produced, regardless of the quality of that source water. Virtually any type of water-based therapeutic solution can be produced by this system in any location from any water source.

Without the preliminary purification component and Disinfection component the extended capability of the PGW component would be markedly restricted. Through the combination of these components and full continuum of preventative to therapeutic water and solution can be produced.

What is claimed is:

1. An apparatus comprising:
   a preliminary purification component;
   a UV disinfection component; and
   a pharmaceutical grade water preparation (PGW) component;
   wherein the apparatus is configured to pass water once through each of said components before the water exits the apparatus as pharmaceutical grade water;
   wherein the disinfection component further comprises a UV lamp air-suspended over feed water that flows under the operation of gravity within the disinfection component.

2. The apparatus of claim 1, further comprising a drug pack.

3. The apparatus of claim 2, wherein the drug pack comprises:
   a housing defining a fluid flow path therethrough; and
   at least one reagent bed within the housing along the fluid flow path, the reagent bed including dry reagents in proportions suitable for peritoneal dialysis.

4. The apparatus of claim 3, further comprising a compression component adjacent the reagent bed.

5. The apparatus of claim 4, wherein the compression component comprises a compressible foam member.

6. The apparatus of claim 4, wherein the compression component is positioned within the fluid flow path, and comprises an open cell compressible foam member.

7. The apparatus of claim 4, wherein the compression component comprises a coiled spring.

8. The apparatus of claim 4, wherein a single reagent bed is compressed between an upstream compression component and a downstream compression component.

9. The apparatus of claim 8, wherein the reagent bed is confined between an upstream reagent restraint, positioned between the upstream compression component and the reagent bed, and a downstream reagent restraint, positioned between the downstream compression component and the reagent bed.

10. The apparatus of claim 8, wherein the reagent bed includes dry forms of electrolyte salts, dextrose, and a buffer.

11. The apparatus of claim 3, wherein a first reagent bed is separated from a second reagent bed within the housing.

12. The apparatus of claim 11, wherein the first reagent bed is separated from the second reagent bed by a porous, intermediate compression component.

13. The apparatus of claim 12, wherein the first reagent bed is further separated from the second reagent bed by at least one reagent restraint having a porosity less than the reagent particulate size in the reagent beds.

14. The apparatus of claim 11, wherein the first reagent bed contains reagents unstable in prolonged contact with the second reagent bed.

15. The apparatus of claim 14, wherein the first reagent bed comprises a bicarbonate, and the second reagent bed comprises a calcium salt.

16. The apparatus of claim 14, wherein the first reagent bed is downstream of the second reagent bed.

17. The apparatus of claim 1, wherein the UV disinfection component comprises a UV lamp that emits UV light in the wavelength range 240 to 280 nanometers (nm).

18. The apparatus of claim 1, wherein the preliminary purification component further comprises a depth filtration component.

19. The apparatus of claim 1, wherein the preliminary purification component further comprises an organic chemical reduction component.

20. The apparatus of claim 1, wherein the preliminary purification component further comprises a deionization component.

21. The apparatus of claim 1, wherein the disinfection component further comprises an inlet port provided at a specific diameter limiting inlet water flow to an inlet water flow rate.

22. The apparatus of claim 21, wherein the inlet port is about 1.5 cm in diameter when the inlet water flow rate is about 15 liters/minute.

23. The apparatus of claim 21, wherein the inlet port is about 3 cm in diameter when the inlet water flow rate is about 60 liters/minute.

24. The apparatus of claim 1, wherein the disinfection component further comprises a treatment chamber tray, the tray comprising angled sides to ensure uniform UV exposure.

* * * * *